(12) United States Patent
Lin et al.

(10) Patent No.: US 6,193,931 B1
(45) Date of Patent: *Feb. 27, 2001

(54) CONTAINER MONITORING SYSTEM

(75) Inventors: Szu-Min Lin, Laguna Hills; Paul Taylor Jacobs, Trabuco Canyon, both of CA (US)

(73) Assignee: Ethicon, Inc., Skillman, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/172,360

(22) Filed: Oct. 14, 1998

Related U.S. Application Data

(63) Continuation-in-part of application No. 08/934,496, filed on Sep. 19, 1997, now Pat. No. 5,834,313.

(51) Int. Cl.[7] .............................. A61L 2/16; G01N 31/22; C12Q 1/22
(52) U.S. Cl. .................. 422/28; 422/34; 422/36; 422/37; 422/300; 436/1; 436/126; 436/128; 435/31; 435/287.4
(58) Field of Search ................... 436/1, 126, 127, 436/128; 422/26, 28, 34, 61, 36, 37, 292, 300; 435/31, 287.4

(56) References Cited

U.S. PATENT DOCUMENTS

| | | | | |
|---|---|---|---|---|
| 3,960,670 | * | 6/1976 | Pflug | 435/31 |
| 4,580,682 | * | 4/1986 | Gorski et al. | 206/569 |
| 5,160,700 | * | 11/1992 | Anderson et al. | 422/34 |
| 5,486,459 | * | 1/1996 | Burnham et al. | 435/31 |
| 5,552,320 | * | 9/1996 | Smith | 435/287.4 |
| 5,834,313 | * | 11/1998 | Lin | 436/1 |

* cited by examiner

*Primary Examiner*—Randy Gulakowski
*Assistant Examiner*—LaToya I. Cross

(57) ABSTRACT

A sterilization system using a sterilization process monitoring device which is capable of indicating the efficacy of the sterilization process in an enclosed sterilization container while still maintaining the sealed state of the sterilization container. The process monitoring device comprises at least one biological indicator and/or at least one chemical indicator. Upon completion of the sterilization cycle, the process monitoring device can be advantageously removed from the system to determine chemical and/or biological efficacy of the sterilization process. The removal of the biological and/or chemical indicators does not disturb the sterilized state of the articles inside the sterilization container.

20 Claims, 13 Drawing Sheets

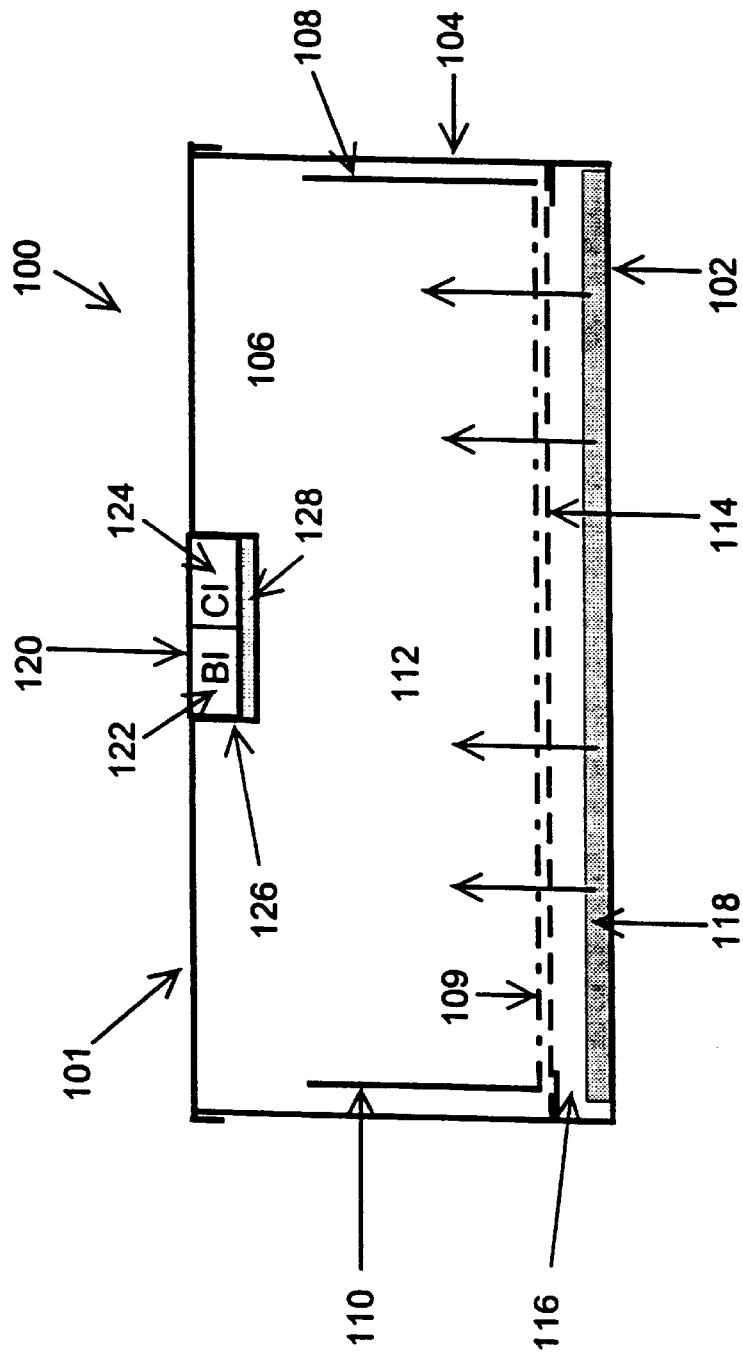
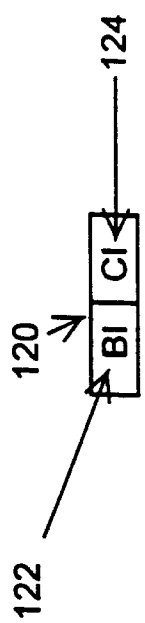
Figure 1A
Figure 1B

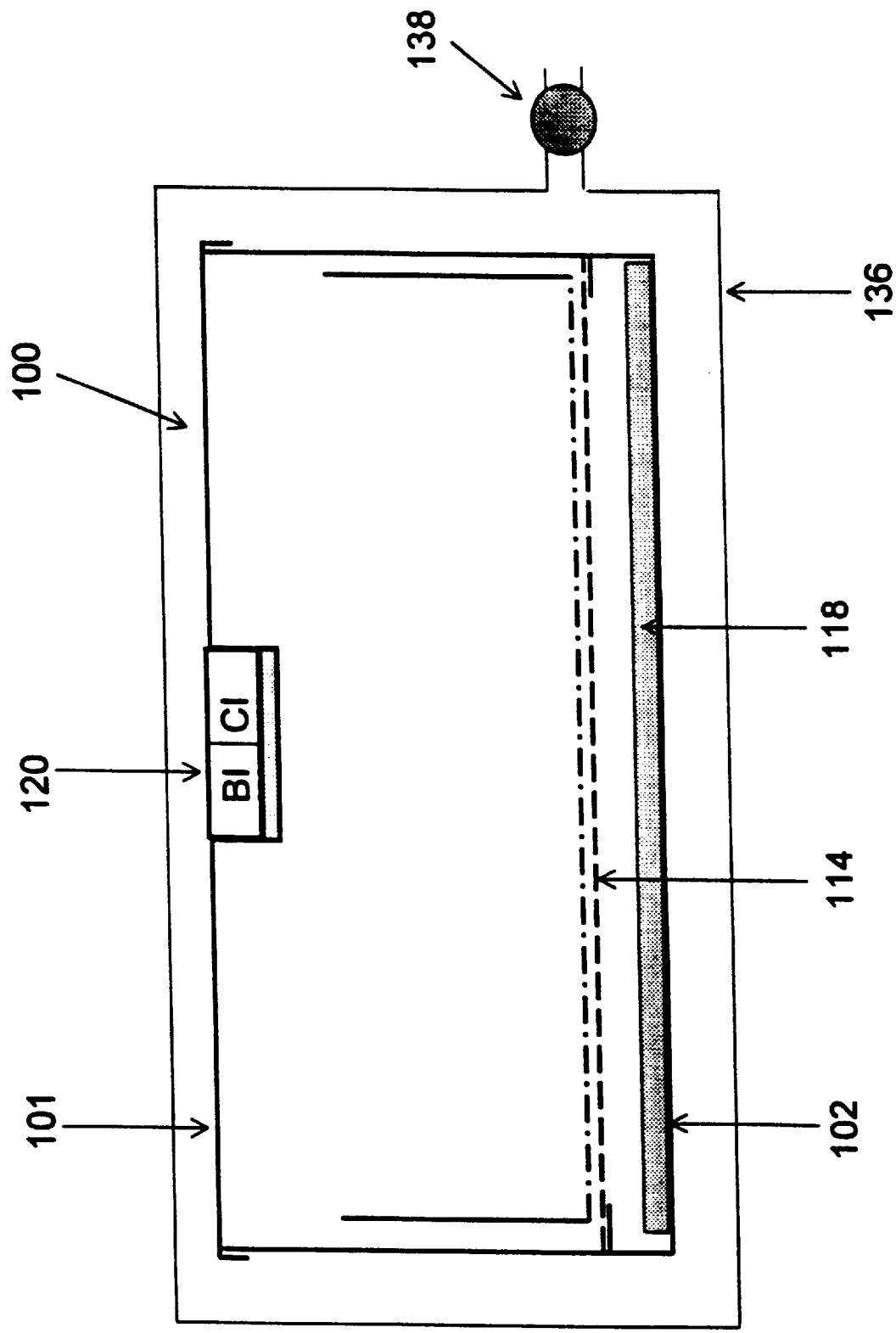

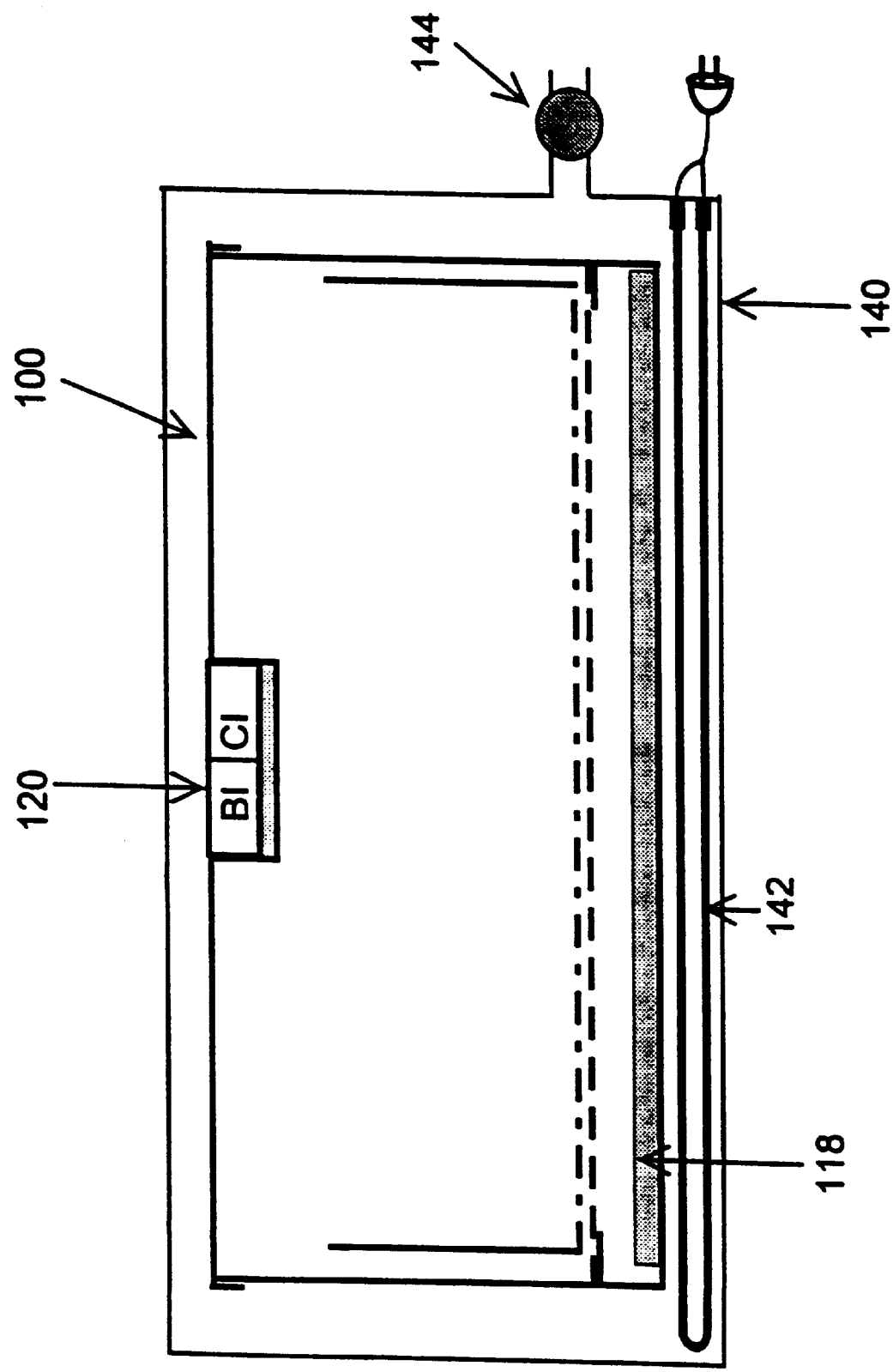

CONTAINER MONITORING SYSTEM

PRIORITIES CLAIMED

This application is a continuation-in-part of U.S. patent application Ser. No. 08/934,496 filed Sep. 19, 1997 now U.S. Pat. No. 5,834,313.

BACKGROUND OF THE INVENTION

1. Field of the Invention

The present invention generally relates to sterilization processes, and more particularly, to the techniques for monitoring the efficacy of a container system.

2. Description of the Related Art

A sterilization process generally involves in exposing the articles to be sterilized to a sterilizing medium that can kill bacterial microorganisms. Such processes are performed in sterilization chambers. The articles to be sterilized are often delivered to the sterilization chambers within a sterilization container in which the articles are both sterilized and subsequently stored in their sterilized state. In some instances, articles are merely disinfected, but are often nevertheless delivered within a container.

The containers are generally permeable to a sterilizing medium so that the sterilizing medium may enter the container during the sterilization process. A sterilizing medium may be a sterilant gas or vapor (e.g., hydrogen peroxide vapor) released by a sterilant source which is placed into or delivered into the sterilization container. As used hereinafter, the terms "gas" and "vapor" are used interchangeably. Such gas permeable containers may, for example, include pouches made of gas permeable materials or rigid trays wrapped with gas permeable wraps. In fact, a sterilization container may be configured as a sealable rigid container having ports to deliver a sterilant after the container has been sealed. In all above examples, however, the sterilization containers prevent the entry of the microorganisms into the container and thereby maintain the sterilized state of the articles therein.

In modem medical and dental practice, it is important to monitor the efficacy of the sterilization processes. That is, at the end of the sterilization cycle, it must be verified that all of the articles have been adequately exposed to the sterilizing medium and the existing microorganisms have been killed. Conventional sterilization processes commonly have two underlying monitoring devices that address such concerns, namely, biological indicators and chemical indicators. A biological indicator (BI) is a type of device having a source of microorganisms. In this context, the source of microorganisms refers to a predetermined concentration of microorganisms which are generally impregnated into a paper strip. A biological indicator is used to monitor the sterilization process and determine whether the particular sterilant succeeded in killing all the microorganisms in the load to be sterilized. In practice, the biological indicator is maintained in a gas permeable pack which is made of gas permeable materials. During the sterilization process, the biological indicators are conventionally placed outside the sterilization containers so that the biological indicator can be retrieved without compromising the sterility of the devices within the container. After exposure to the sterilization process, the source of microorganisms is placed in a sterile culture medium and incubated for a pre-determined period of time. Any surviving microorganisms indicates the incompleteness of the sterilization process in the container. One example of such a BI is shown in the Smith, U.S. Pat. No. 5,552,320, issued Sep. 3, 1996, incorporated herein by reference. Alternatively, a source of enzymes which mimic the response of living organisms to the sterilization procedure in a measurable fashion may be substituted for living microorganisms. Examples of this type of BI are shown in the Matner, U.S. Pat. No. 5,073,488 issued Dec. 17, 1991 and the Burnham, U.S. Pat. No. 5,486,459, issued Jan. 23, 1996, each of which are incorporated herein by reference.

On the other hand, chemical indicators (CI) are devices that primarily indicates whether or not the sterilization process cycle is carried out properly to deliver the sterilant to the sterilization chamber. Thus, chemical indicators do not provide a true indication that sterility has been achieved. Chemical indicators contain specific chemical compositions which chemically reacts and change color when exposed to the sterilizing medium. Additionally, chemical indicators may be designed to include and respond to a plurality of sterilization process parameters. For example, a chemical indicator can be designed to indicate or respond to certain sterilant concentrations, humidity, time, temperature, sterilant's pH or pressure.

During conventional sterilization processes, biological and chemical indicators are typically placed outside the gas permeable sterilization containers in which the load of the articles to be sterilized are placed. Upon completion of the sterilization process, containers, which are in their sealed state and with a presumably sterilized load, are often stored for a period of time before the sterilized articles are needed. In such conventional processes, the actual state of the sterilization inside the container is determined by inspecting the indicators located outside the container to determine whether the sterilization has been achieved. However, in practice, this approach has serious drawbacks because these indicators cannot provide accurate information about the sterilization status of the articles in the container. Since the indicators only display the outside readings, there is no way of knowing whether sterilization has occurred inside the container.

An alternative approach utilizes two chemical indicators to overcome the above given drawback. In this approach one of the chemical indicators is placed into the container adjacent to the load of articles. Unfortunately, the problem with this approach is that the actual state of the sterilization can only be determined by opening the container and inspecting the chemical indicator placed inside the container. However, this is also not practical and disturbs the sealed state of the container and the sterility of the devices therein. There also is a possibility that sterilization conditions were not achieved inside the container. Accordingly, throughout the storage period, the actual state of the sterilization process cannot be known.

Some container systems have a clear barrier through which a chemical indicator, but not a biological indicator, can be read. However, such chemical indicators cannot be removed without breaking the barrier. Moreover, in such a system, the chemical indicator is included within the load, so it is exposed to sterilant at the same time as the load. As a result, the chemical indicator may indicate a sterile result, even when portions of the load have not been exposed to sufficient sterilant to achieve sterility.

In view of the foregoing, there is a need for a new monitoring system for sterilization processes which is capable of indicating the state of the sterilization in an enclosed sterilization container while maintaining the sealed state of the sterilization container.

SUMMARY OF THE INVENTION

The aforementioned needs are satisfied by the system of the present invention which comprises a sterilization system using a sterilization process monitoring device which is capable of indicating the efficacy of the sterilization process in an enclosed sterilization container while still maintaining the sealed state of the sterilization container.

A system for monitoring a sterilization or disinfection process according to the present invention comprises a container impermeable to microorganisms and having an interior space to receive articles to be sterilized or disinfected. An antimicrobial source provides an antimicrobial agent to the interior space. At least one indicator indicates a parameter relevant to the sterilization or disinfection process and is detachable from the container. An isolation means between the indicator and the interior space allows fluid communication between the interior space, at least during the sterilization or disinfection process, and inhibits the ingress of microorganisms therethrough, at least after the indicator has been detached from the container, whereby the indicator can be detached from the container without potentially exposing the interior space to microorganisms.

Preferably, the antimicrobial source comprises an ingress means, such as for instance a valve or a vapor permeable yet microorganism impermeable material, for allowing the antimicrobial agent ingress to the container during a sterilization process. Alternatively, a supply of the antimicrobial agent can be provided within the interior space. For instance, a liquid supply of hydrogen peroxide solution can be provided which upon reducing the pressure in the interior space vaporizes to sterilize the article or articles with hydrogen peroxide vapor. Solid sources which liberate hydrogen peroxide when heated my also be employed. Other means of liberating an antimicrobial agent may also be employed, such as a chemical reaction or the like.

The isolation means may comprise a valve. Preferably, the valve would close automatically as the indicator is detached but a manually closable valve is also contemplated. Alternatively, the indicator can communicate with the interior space through a vapor permeable, microorganism impermeable material.

Preferably, the indicator is a biological indicator, and it preferably contains test microorganisms. The indicator may be a chemical indicator indicative of a parameter relating to the antimicrobial agent. For instance, the indicator may register the presence of hydrogen peroxide or the level of exposure thereto.

A method of monitoring a disinfection or sterilization procedure according to the present invention comprises placing an article to be disinfected or sterilized into an interior space of a container impermeable to microorganisms; placing at least one indicator into fluid communication with the interior space while performing the disinfection or sterilization procedure by providing an antimicrobial agent in the interior space; detaching the indicator from the container while keeping the interior space isolated from microorganisms; and indicating by the indicator a parameter relevant to the disinfection or sterilization procedure.

The antimicrobial agent preferably is selected from the group consisting of: steam, hydrogen peroxide, peracetic acid, chlorine dioxide, glutaraldahyde and ethylene oxide.

These and other objects and advantages of the present invention will become more fully apparent from the following description taken in conjunction with the accompanying drawings.

BRIEF DESCRIPTION OF THE DRAWINGS

FIG. 1A is a schematic view of a system comprising a sterilization container with an attachable process monitoring device;

FIG. 1B is a schematic detail view of the attachable process monitoring device;

FIG. 4 is a schematic view of a fourth embodiment of the system wherein the sterilization container is placed into a vacuum chamber;

FIG. 5 is a schematic view of a fifth embodiment of the system wherein the sterilization container is placed into a vacuum oven;

DETAILED DESCRIPTION OF THE PREFERRED EMBODIMENT

Figure 1C:
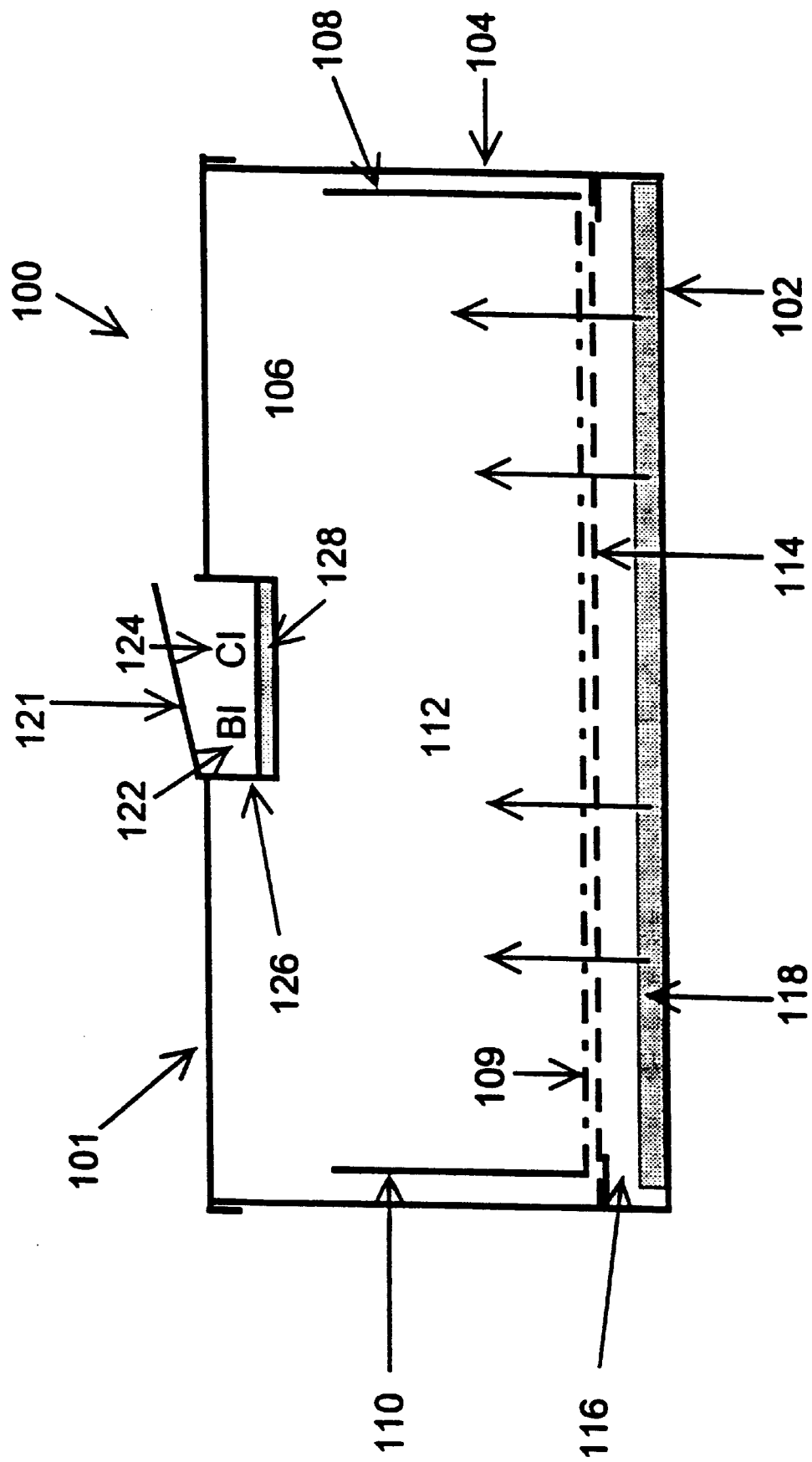
FIG. 1C is a schematic view of a modified form of the first embodiment of the system in which a process monitoring device is provided within an openable housing.

As an improvement to conventional monitoring systems for sterilization processes, the process of the preferred embodiments are preferably capable of indicating the efficacy of the sterilization process in an enclosed sterilization container while still maintaining the sealed state of the sterilization container. Reference will now be made to the drawings wherein like numerals refer to like parts throughout.

As illustrated in FIG. 1, sterilization system of the preferred embodiment comprises a first container 100. In the preferred embodiment, the first container 100 is preferably a rigid enclosed container comprising a top portion 101, a bottom portion 102 and a peripheral wall 104 which is preferably perpendicularly attached to the periphery of the bottom portion 102.

Preferred materials for manufacturing the solid container 100 may be metals or polymers such as aluminum, stainless steel or plastics. The bottom portion 102 and the peripheral wall 104 define a container housing 106. The container housing 106 may be preferably configured and dimensioned to receive at least one optional second container 108. The second container 108 may be configured as a tray having a perforated bottom 109 and a peripheral wall 110. The perforated bottom 109 and the peripheral wall 110 of the tray 108 define a second housing 112 to accommodate articles (not shown) to be sterilized. Inside the container housing 106, the tray 108 may be removably placed on an optional rack 114 which may be made of a perforated plate. Preferably, the rack 114 is removably attached to the inside of peripheral wall 104 so as to stay elevated from the bottom portion 102 of the container and so as to define a sterilant housing 116. A sterilant source 118 may be further placed into the sterilant housing 116 to produce a sterlizing medium such as a vapor sterilant. An exemplary sterilant source may be liquid peroxide, solid hydrogen peroxide complex and peracetic acid. A variety of solid peroxide complexes are described in allowed U.S. patent application Ser. No. 08/549,425, filed Oct. 27, 1995, the complete disclosure of which is hereby incorporated by this reference thereto. The top portion 101 of the container 100 comprises a removable container lid which seals the container housing 106 when closed.

As illustrated in FIGS. 1A–1B, in the preferred embodiment, a cartridge 120 comprising at least one process monitor device may be removably positioned onto the lid 101 of the container 100. In accordance with the principles of the present invention, these process monitor devices may comprise at least one biological indicator 122 and/or at least one chemical indicator 124. Either or both of these indicators can be provided with a unique identifier, such as a serial number, which pairs the indicator with the container. Thus, the container can be provided with the same identifier in order to pair it with the indicator.

As previously noted in the background section, the biological indicator 122 is kept in a gas permeable pack which permit the passage of the sterilizing gas but not the passage of microorganisms. In the preferred embodiment, such packs may, for example, be made of spun-bond polyethylene (e.g. Tyvek™) or non-woven polypropylene wrap (e.g. CSR-wrap) materials. The cartridge 120 containing the biological and the chemical indicators 122 and 124 may be placed into a cartridge holder 126. The bottom layer of the cartridge 120 can optionally comprise a gas permeable material. The cartridge holder 126 may be configured to have a recessed cavity having a bottom 128 portion and downwardly extending into the container housing 106. The cartridge holder 126 may be dimensioned to receive at least one cartridge 120. In the preferred embodiment, the bottom portion 128 of the cartridge holder 126 is made of above-mentioned gas permeable materials (e.g., Tyvek™ or CSR-wrap) so that the sterilant vapor from the housing 106 can pass through the gas permeable material and reach indicators 122 and 124. The cartridge 120 may be secured in cartridge holder 126 by employing a number of fastening mechanisms such as snap-on type connectors or the like. However, with possible modifications in the cartridge 120 and the cartridge holder 126, the cartridge 120 may be secured to the holder 126 by a twist or a screw type of connector as well.

In the process of the preferred embodiment, the vapor sterilant such as hydrogen peroxide vapor diffuses through the rack 114 and the perforated bottom 109 of the tray 108 (in the direction of the arrows) and thereby contacting the articles and filling the container housing 106. While the sterilization process progresses, the sterilant vapor also diffuses through the gas permeable membrane 128 and subsequently into the cartridge 120 having the biological and/or chemical indicators 122 and 124. The sterilant vapor entering the cartridge 120 exposes indicators to the same sterilizing environment encountered by the articles in the tray 108. At this point, it is highly desirable that, on the container 100, the gas permeable membrane 128 of the holder 126 be accommodated at a farthest possible location from the sterilant source 118. As a result of this, the articles in the container 100 are treated with the sterilant vapor before the sterilant vapor diffuses through the gas permeable membrane 128. Since the indicators 122 and 124 are the last place for sterilant vapor to reach, they provide an accurate method of monitoring the sterilization status of the articles inside the container 100.

The sensitivity of the biological indicator and chemical indicator can be adjusted by adding features well known to those having ordinary skill in the art. A variety of such features are known which slow down the diffusion of sterilant. One example would be the Sterrad® Biological Indicator (BI) Test Pack, available from Advanced Sterilization Products (Irvine, Calif.).

In the present embodiment, upon completion of the sterilization cycle the cartridge 120 may be removed from the cartridge holder 126 to determine chemical and biological efficacy of the sterilization process. As opposed to prior art, however, the biological and/or chemical indicators can be removed from the container 100 without disturbing the sterilized state of the articles inside the sterilization container 100. Since the gas permeable layer 128 only allows the passage of the sterilant vapor, removal of the cartridge 120 from the holder 126 will not break the seal of the container 100.

Referring now to FIG. 1C, there is shown a modified form of the embodiment shown in FIG. 1A. In this embodiment, the biological indicator 122 and/or chemical indicator 124 are placed into a housing 126 with an openable or removable door 121. This modified form of this first embodiment can otherwise be constructed and used in accordance with the description provided above.

In addition, it is particularly advantageous to use the biological and chemical indicators 122 and 124 in separate cartridges. In such case, the chemical indicator may be furnished with a translucent or clear window which can display a written message, such as "PROCESSED", or a symbol when the sterilization cycle is completed. Therefore, when the biological indicator is removed for detection, the chemical indicator may remain on the container and display the message to avoid any confusion during the storage. Alternatively, if the sterilization process uses more than one sterilant source, the number of chemical indicators can be increased accordingly. For example, if two chemicals are used as sterilant sources, the cartridge holder can be configured to have two chemical cartridges indicators and one or more biological indicator cartridges.

Figure 2:
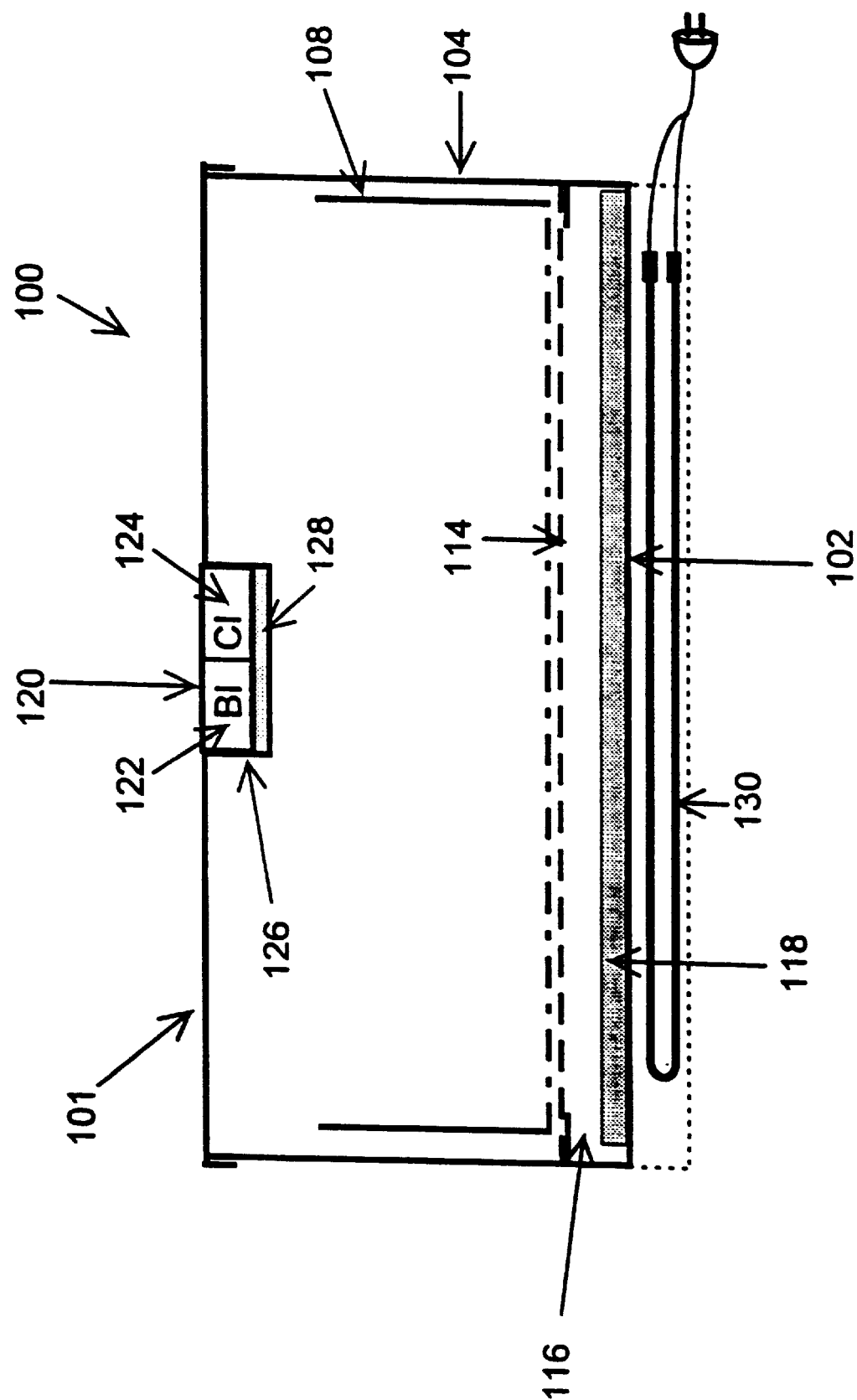
FIG. 2 is a schematic view of a second embodiment of the system wherein the sterilization container comprises a heating source.

As will be explained more fully in the following embodiments, the release of the sterilant gas can be enhanced using heat or vacuum. FIGS. 2–9C illustrates alternative embodiments of the present invention. FIG. 2 illustrates a second embodiment of the sterilization system comprising the sterilization container 100 and a heat source 130. In accordance with the principles of the present invention, the heat source 130 may be configured as a part of the container 100 or positioned adjacent to the container 100 without being a part of the container 100. In this embodiment, the heat source 130 may be a heat element comprising a resistant wire which is attached to the bottom portion 102 of the sterilization container 100. Heat from the heat element 130 enhances the vaporization of the sterilant source 118 in the sterilant housing 116 and thereby enhancing the sterilization of the articles in the container 100.

Figure 3:
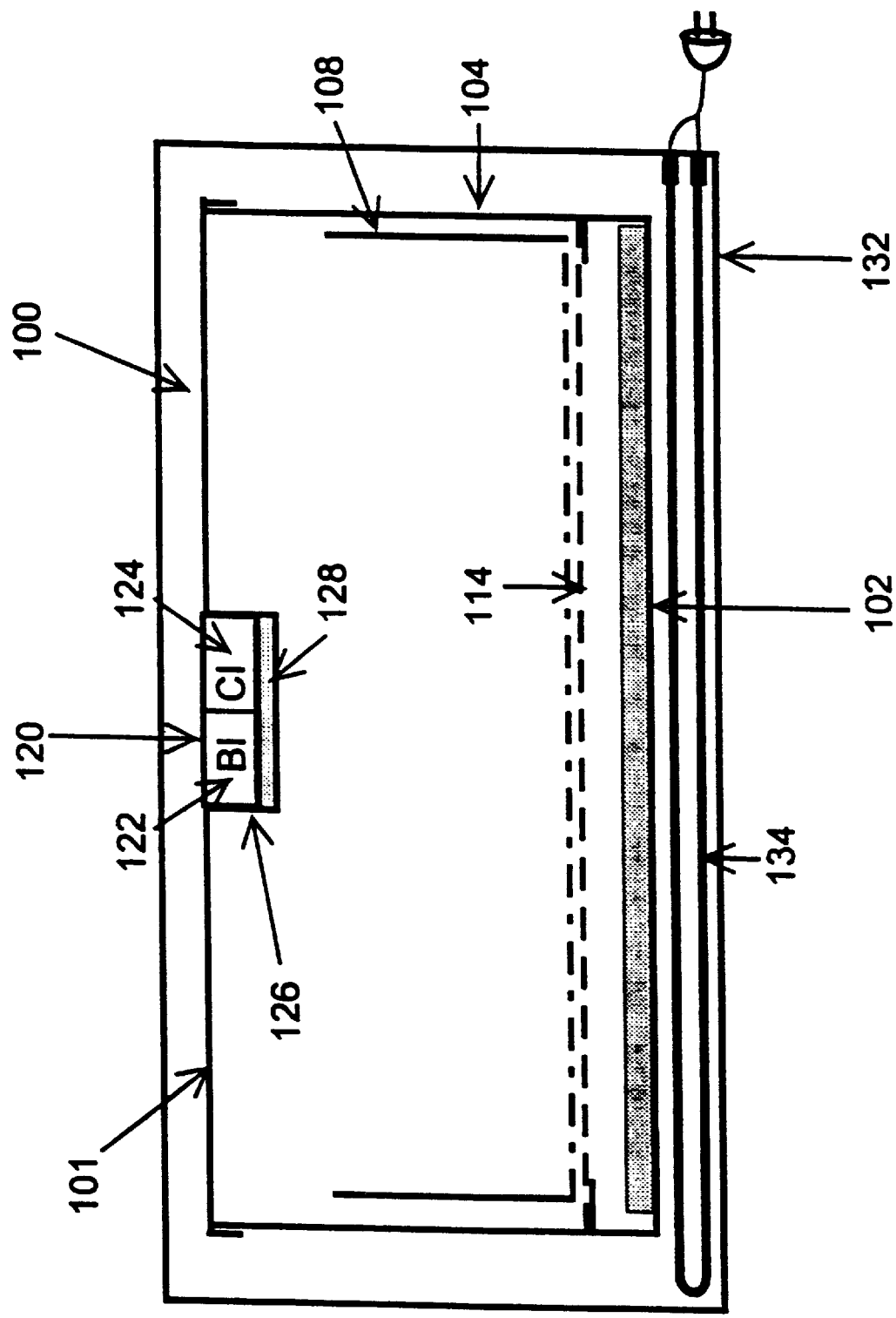
FIG. 3 is a schematic view of a third embodiment of the system wherein the sterilization container is placed into an oven.

FIG. 3 illustrates a third embodiment of the sterilization system comprising the sterilization container 100 placed into a third container 132. The third container 132 may be an oven having a heat source 134. In accordance with the principles of the present invention, the heat source 134 of the oven 132 may comprise infrared (IR) heating, radio frequency (RF) heating, microwave heating or resistant heating by heating elements. In the preferred embodiment, heating is provided by the heating elements 134.

FIG. 4 illustrates a fourth embodiment of the sterilization system comprising the sterilization container 100 placed into a vacuum chamber 136 which is connected to a vacuum source (not shown) through a vacuum valve 138. The vacuum may also be used to enhance the vaporization of the sterilant source 118. Once the sterilization process is completed, the vacuum may also be used to remove the sterilant residues left on the articles.

FIG. 5 illustrates a fifth embodiment of the sterilization system comprising the sterilization container 100 placed into a vacuum oven 140. The vacuum oven is connected to a vacuum source (not shown) through a vacuum valve 144. The vacuum oven also comprises a heat source 142. In this embodiment, the combined effect of the vacuum and the heat enhances the vaporization of the sterilant source 118.

Figure 6A:
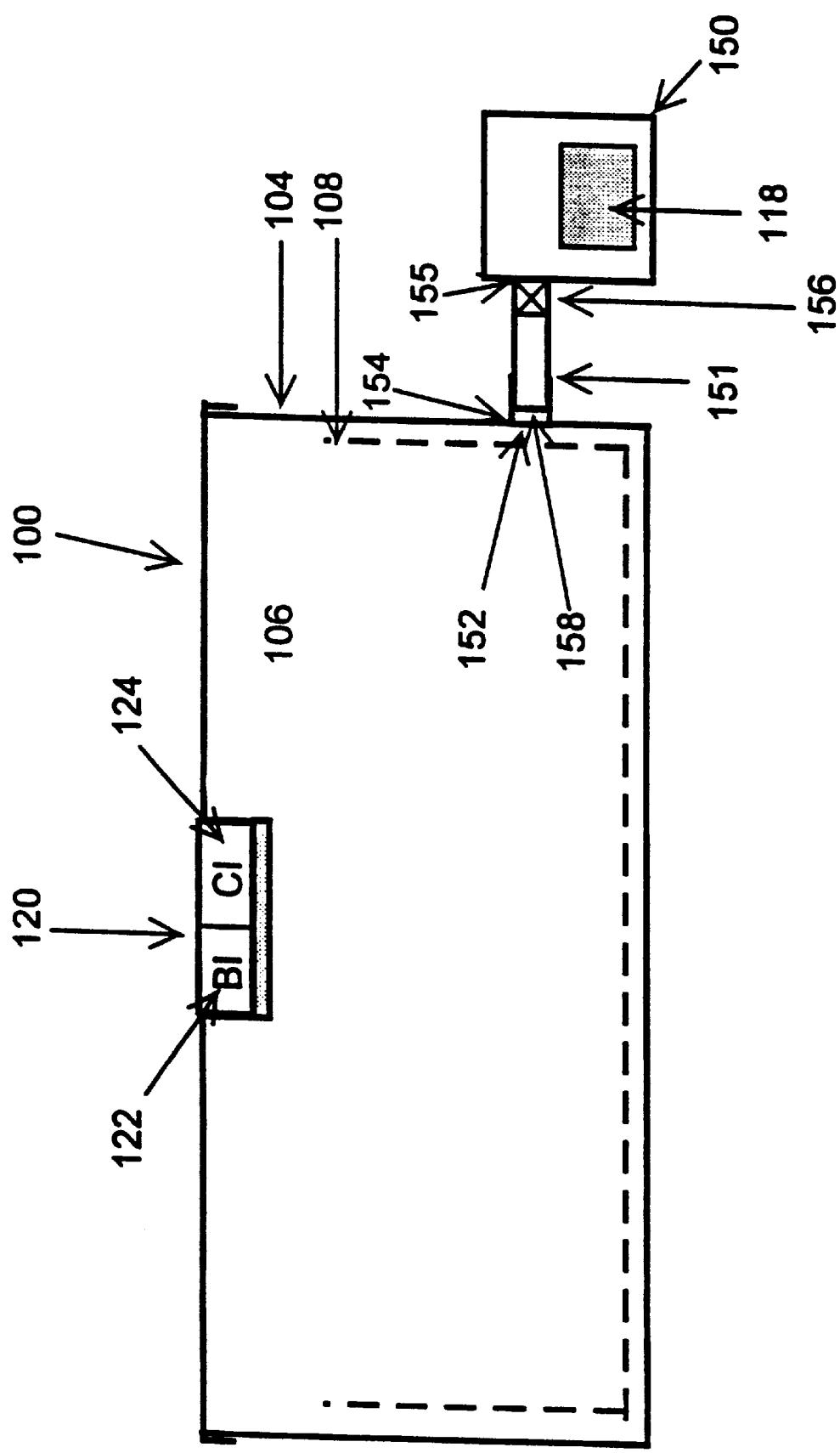
FIG. 6A is a schematic view of a sixth embodiment of the system wherein the sterilization container comprises a separate sterilant enclosure.

FIG. 6A illustrates a sixth embodiment of the sterilization system comprising the sterilization container 100. In this embodiment, the sterilization container 100 is modified to include an attachable sterilant enclosure 150 with the sterilant 118. Therefore, in this embodiment, the rack 114 and the sterilant housing 116 (See FIGS. 1A–5) shown in the previous embodiments are excluded. Accordingly, the sterilization container 100 is connected to the sterilant enclosure 150 by a connector 151. In this embodiment, a first end 154 of the connector 151 is connected to an opening 152 on the peripheral wall 104, while a second end 155 of the connector 151 is connected to the sterilant enclosure 150 through an optional valve 156 on the enclosure 150. A gas permeable membrane 158 further covers the opening 152 so that when the sterilant enclosure 150 is detached from the container 100, the sterility of the load in the container housing 106 is maintained. In the process of the present embodiment, the sterilant vapor from the sterilant source 118 passes through the valve 156 and gas permeable membrane 158 and enters the container 100 for sterilizing articles. For better diffusion, the inner tray 108 can have perforated walls. Similar to the previous embodiments, the biological and chemical indicators 122 and 124 can be attached to or detached from the container 100 without disturbing the sterility of the articles in the container 100.

Figure 6B:
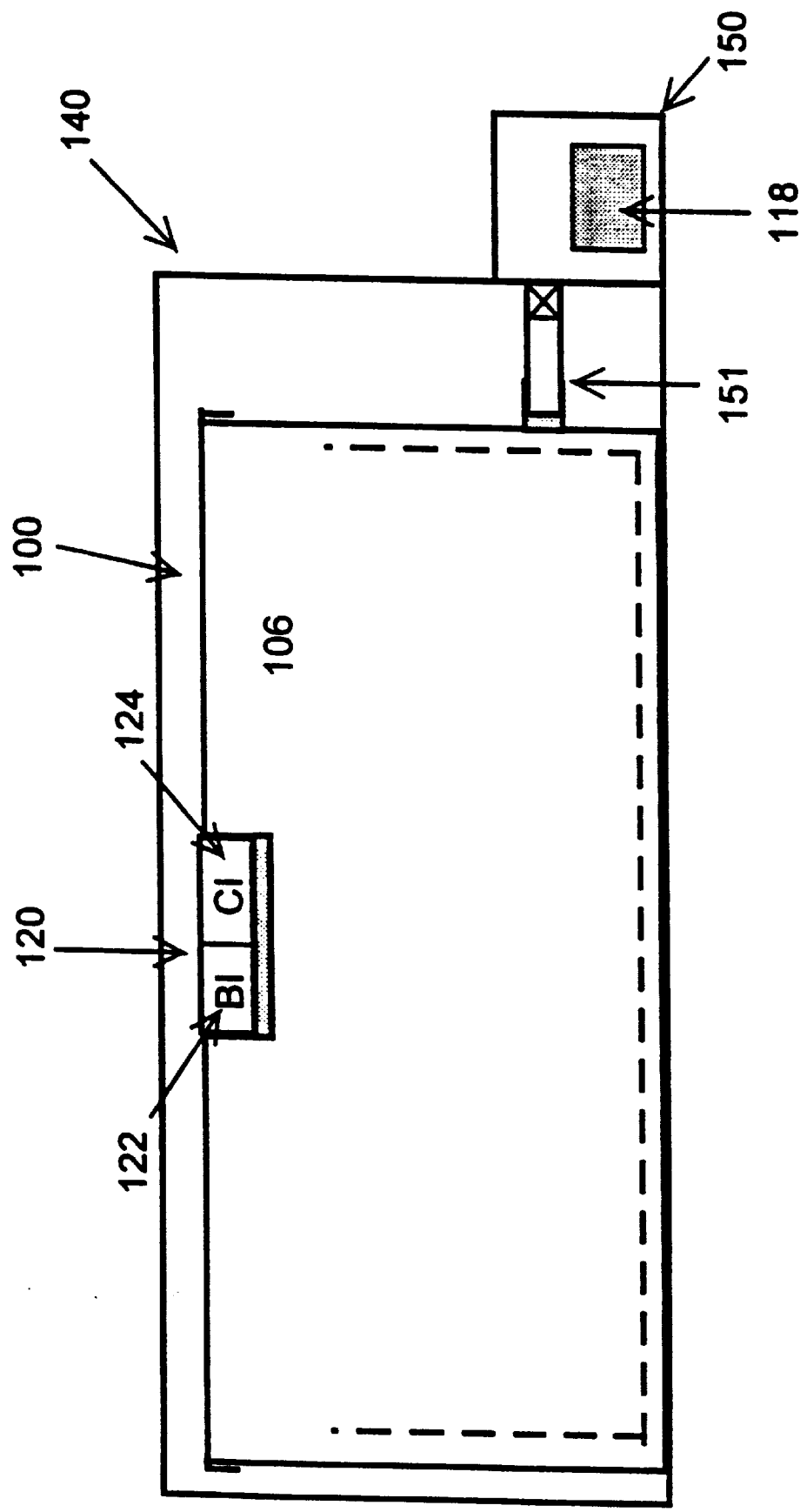
FIG. 6B is a schematic view of the system shown in FIG. 6A wherein the sterilization container with the separate sterilant enclosure is placed into a vacuum oven.

Within the scope of this invention, it will be appreciated that the present embodiment may also comprise all the features and options of the previous embodiments. For example, as in the second embodiment, the sterilant enclosure 150, as attached to the container 100, may be heated by a heat source to enhance the vaporization of the sterilant source 118 (See FIG. 2). Similar to the third, the fourth and the fifth embodiments, the container can be placed into a third container which may be an oven 132, vacuum chamber 136 or a vacuum oven 140 (See FIGS. 3–5). In all above embodiments, after the sterilization the sterilant enclosure 150 may be detached from the container 100 for storage purposes. Similarly, by suitable modifications in the oven 132, the vacuum chamber 136 and the vacuum oven 140, the sterilant enclosure may be integrated with the containers 132, 136 and 140. As illustrated in FIG. 6B, for example, when the container 100 is placed into the third container, such as a vacuum oven 140, the sterilant enclosure 150 is connected to the container 100 through conductor 151 as in the manner shown in FIG. 6B. The enclosure 150 can be heated to a different temperature than the vacuum oven 140.

Figure 7:
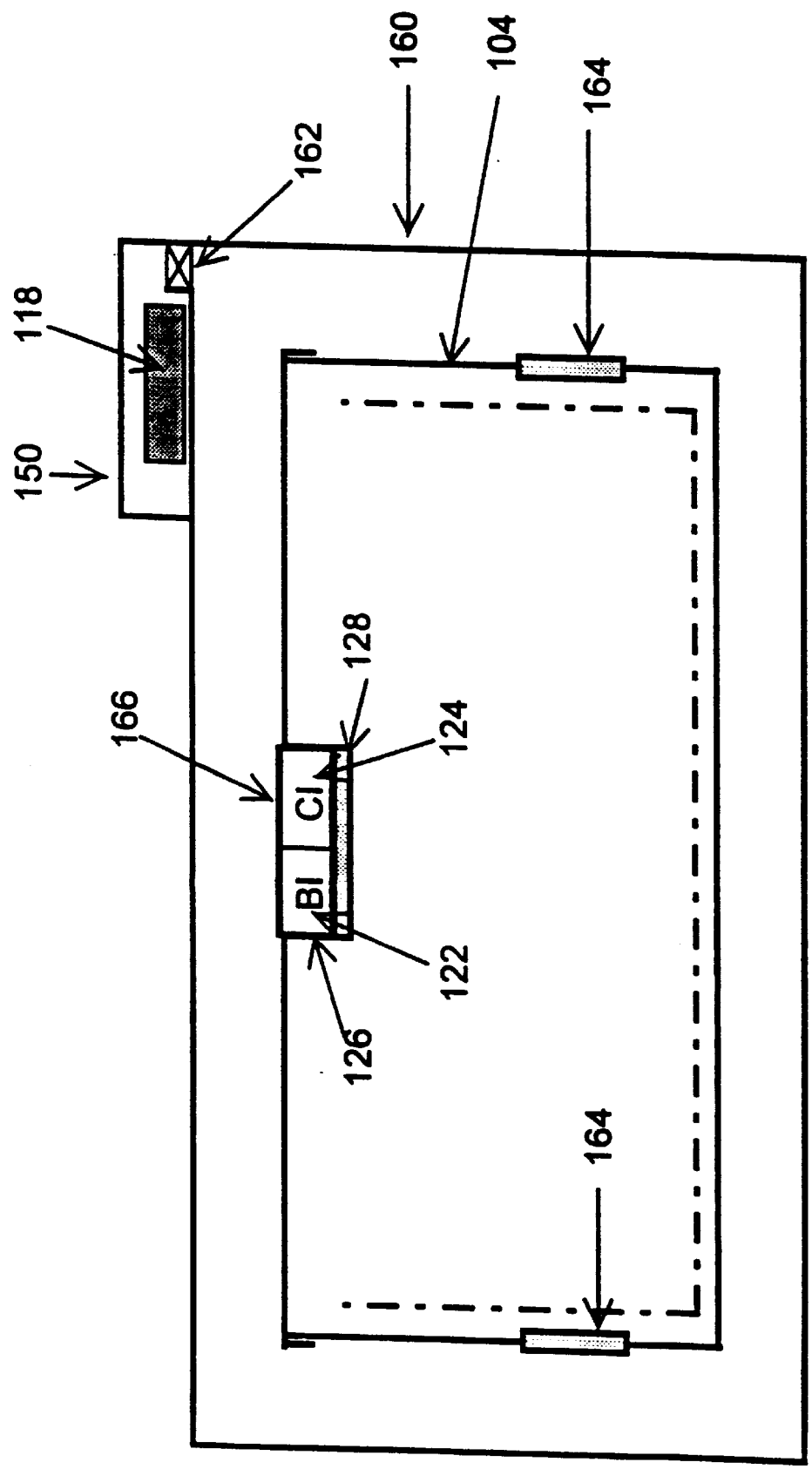
FIG. 7 is a schematic view of a seventh embodiment of the system wherein the sterilization container is placed into another container having an attached sterilant enclosure.

FIG. 7 shows a seventh embodiment of the sterilization system comprising the sterilization container 100 placed into a third container 160 and the enclosure 150 is attached to the container 160, such as by being an integrated part thereof. However, as opposed to previous embodiment, in this embodiment there is no direct connection between the sterilant enclosure 150 and the sterilant container 100. A number of gas permeable membrane covered inlets 164 are positioned on the peripheral wall 104 of the container 100. Further, top of the cartridge holder 126 may be sealed with a removable gas impermeable material 166 so as to expose indicators 122 and 124 only to the sterilant vapor diffusing through the gas permeable membrane 128. An exemplary gas impermeable material can be Mylar, metal foil, glass or adhesive tape. In the process of this embodiment, the sterilant gas first diffuses into the container 160 through inlet 162 and fills the container 160. The inlet 162 can be configured as a valve. As the process progresses, the sterilant gas diffuses from the enclosure 150 through the inlet 162 and into the container 160. From the container 160, the gas diffuses through the permeable membrane 164 into the container 100, through the permeable membrane 128 and into the cartridge 120, so as to contact the indicators 122 and 124. At the end of the process cycle, the gas impermeable material can be removed and the cartridge can be taken out for inspecting indicators 122 and 124.

Figure 8:
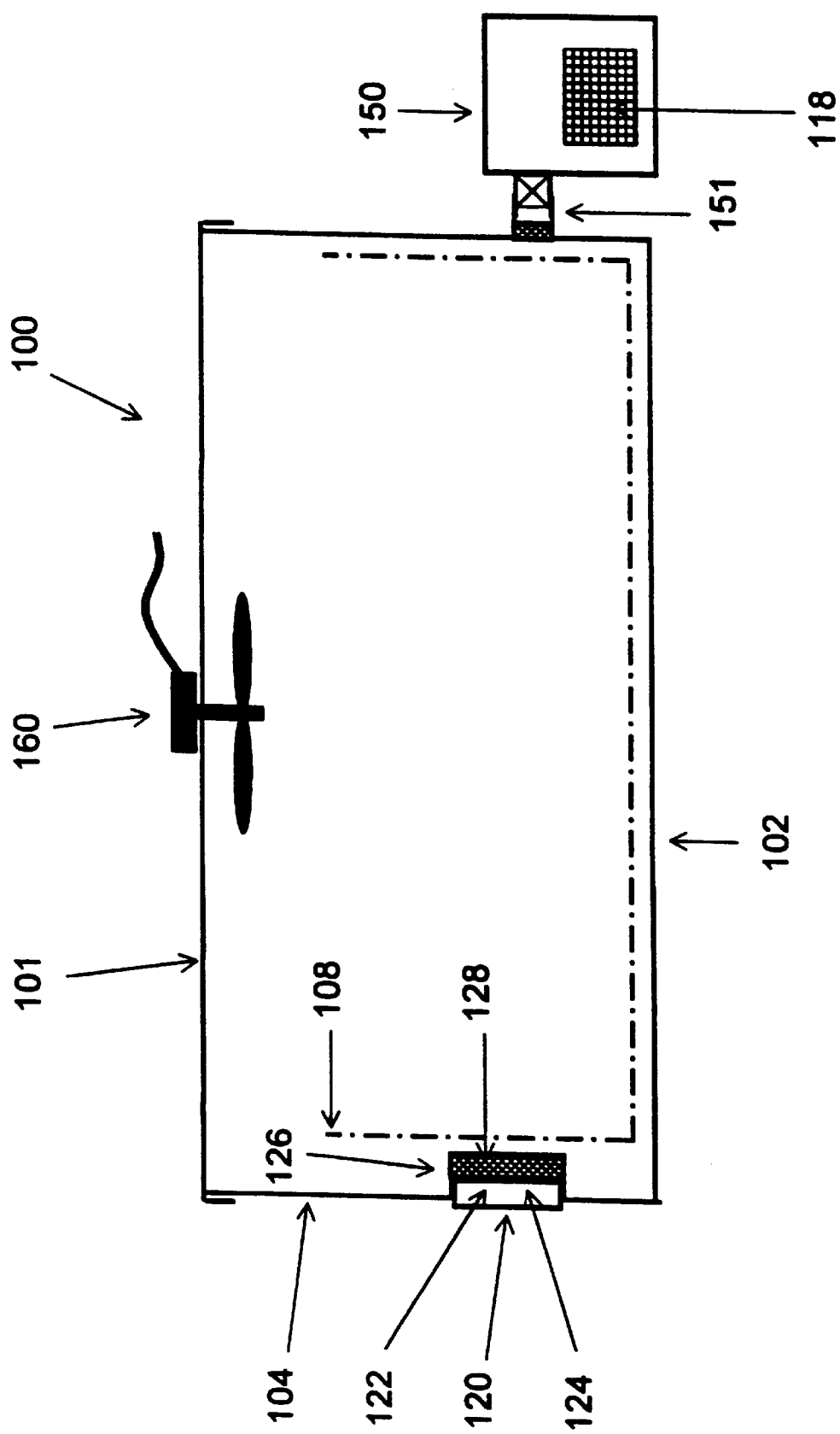
FIG. 8 is a schematic view of an eighth embodiment of the system wherein the separate sterilant enclosure and the process monitor device are placed over the opposite sides of the sterilization container.

As illustrated in FIG. 8, in an eighth embodiment, the sterilization system comprises the sterilization container 100 and the sterilant enclosure 150 as described in the sixth embodiment. In an effort to enhance the accuracy of the information provided from the indicators 122 and 124, in this embodiment, the cartridge holder 126 is positioned at a remotest location from the sterilant enclosure 150 containing sterilant source 118. Referring to FIG. 8, this location is on the peripheral wall 104 and at the opposite side of the container 100. A fan 160 can optionally be provided to circulate sterilant throughout the container 100. As previously explained, since the indicators 122 and 124 are the last place for sterilant vapor to reach, they provide an accurate method of monitoring the sterilization status of the articles inside the container 100.

Figure 9A:
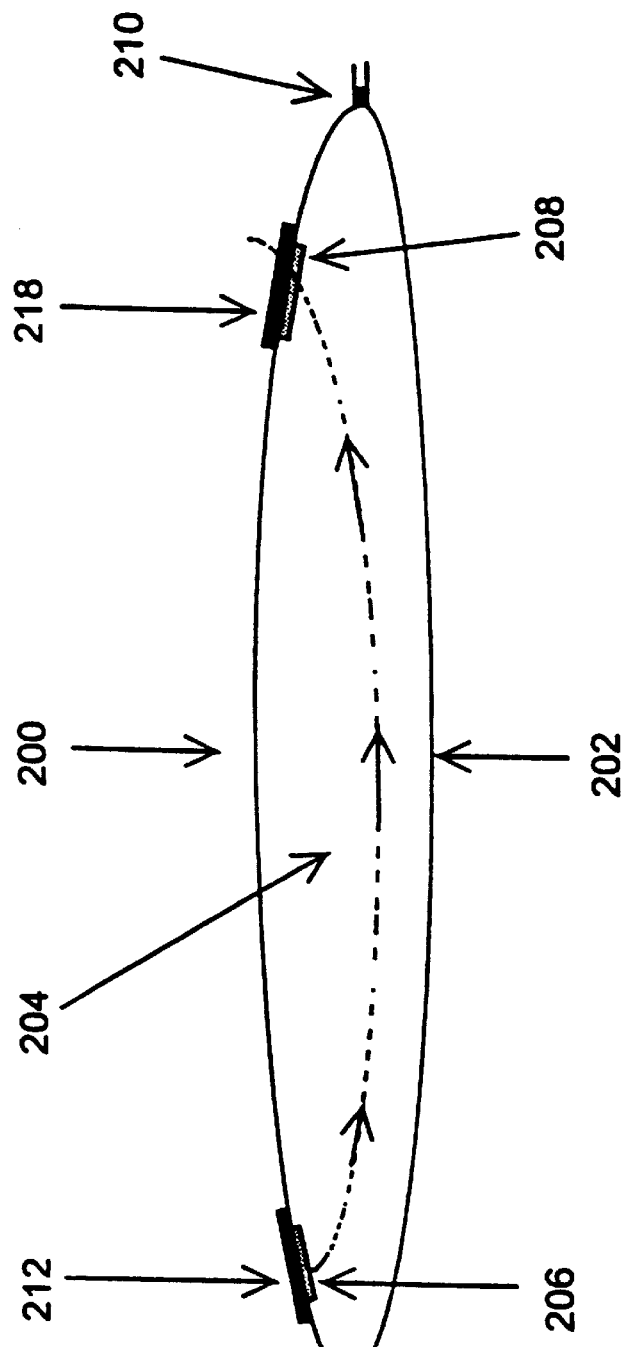
FIG. 9A is a schematic view of an alternative embodiment of the system comprising a flexible container with an attachable process monitor device and an attachable sterilant source cartridge.

As illustrated in FIG. 9A, in a first alternative embodiment, the sterilization system comprises an alternative container 200. In this embodiment, the alternative container 200 is preferably a flexible enclosed container, such as a pouch, which is comprised of a gas impermeable sheet material 202 defining a housing 204 to have articles to be sterilized (not shown). An exemplary gas impermeable sheet material may be preferably Mylar™, metal foil, polymer film materials such as polypropylene or polyethylene films. The flexible container 200 of this invention further comprise a first window 206, second window 208 and an opening 210. The first and second windows 206 and 208 are comprised of gas permeable materials, and preferably positioned at the opposite ends of the pouch 200. Articles to be sterilized are placed into the container 200 through the opening 210. This opening 210 may be a resealable opening for multiple use of the container 200 or may be a non-resealable opening for a single use.

A sterilant source cartridge 212 may be sealably placed onto the first gas permeable window 206 and secured using various fastening mechanisms such as double-sided tape, snap-on connectors or the like. As shown in FIG. 9B, the sterilant source cartridge 212 comprises a gas permeable bottom 216, a gas impermeable top 214 and peripheral side walls 213 defining a sterilant housing 215. For shipping and safe handling purposes, another gas impermeable layer 217 may be removably placed on the layer 216. However, before placing the cartridge onto the window 206, this impermeable layer 217 should be removed. In this embodiment, the gas permeable bottom 216 of the cartridge 212 is preferably sized and shaped to fit over the window 206. Referring to FIG. 9A, when the cartridge 212 is placed onto the gas permeable window 206, the bottom gas permeable layer 216 faces towards the window 206 on the flexible container 200. Therefore, when a sterilant source in the cartridge 212 releases a sterilant vapor, the vapor diffuses via the bottom layer 216 and the window 206 into the container 200 having articles to be sterilized.

Figure 9C:
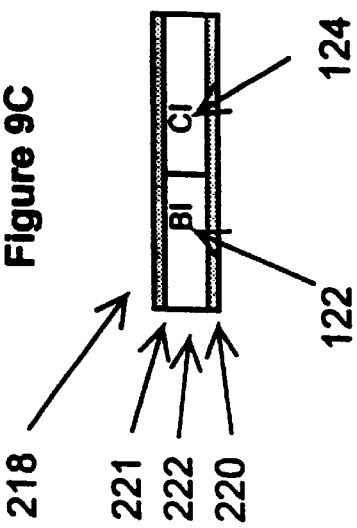
FIG. 9C is a schematic view of the attachable process monitor device.
Figure 9B:
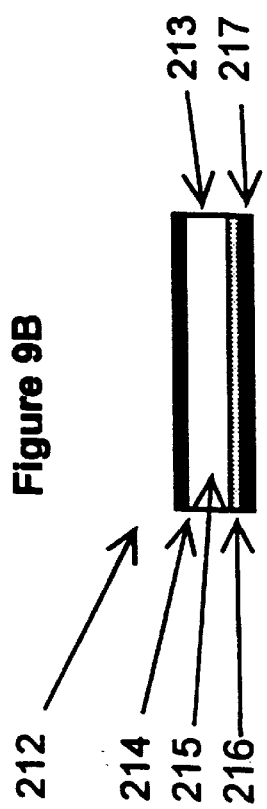
FIG. 9B is a schematic view of the attachable sterilant source cartridge.

As illustrated in FIG. 9C, a process monitoring cartridge 218 comprising the biological and chemical indicators 122 and 124 may be sealably placed onto the second gas permeable window 208, as in the manner described for the sterilant cartridge 212. As shown in FIG. 9C, the process monitoring cartridge 218 is comprised of a gas permeable bottom 220, a gas permeable removable top 221 and a body 222 comprising the biological and/or chemical indicators 122 and 124. In operation, the sterilant gas released from the sterilant cartridge 212 diffuses into the container housing 204 (in the direction of the arrows) and reaches at the monitoring cartridge 218 through the gas permeable window 208. Similar to previous embodiments, the flexible container 200 of the present invention can be also used in the oven 132, the vacuum chamber 136 or a vacuum oven 140.

Figure 9D:
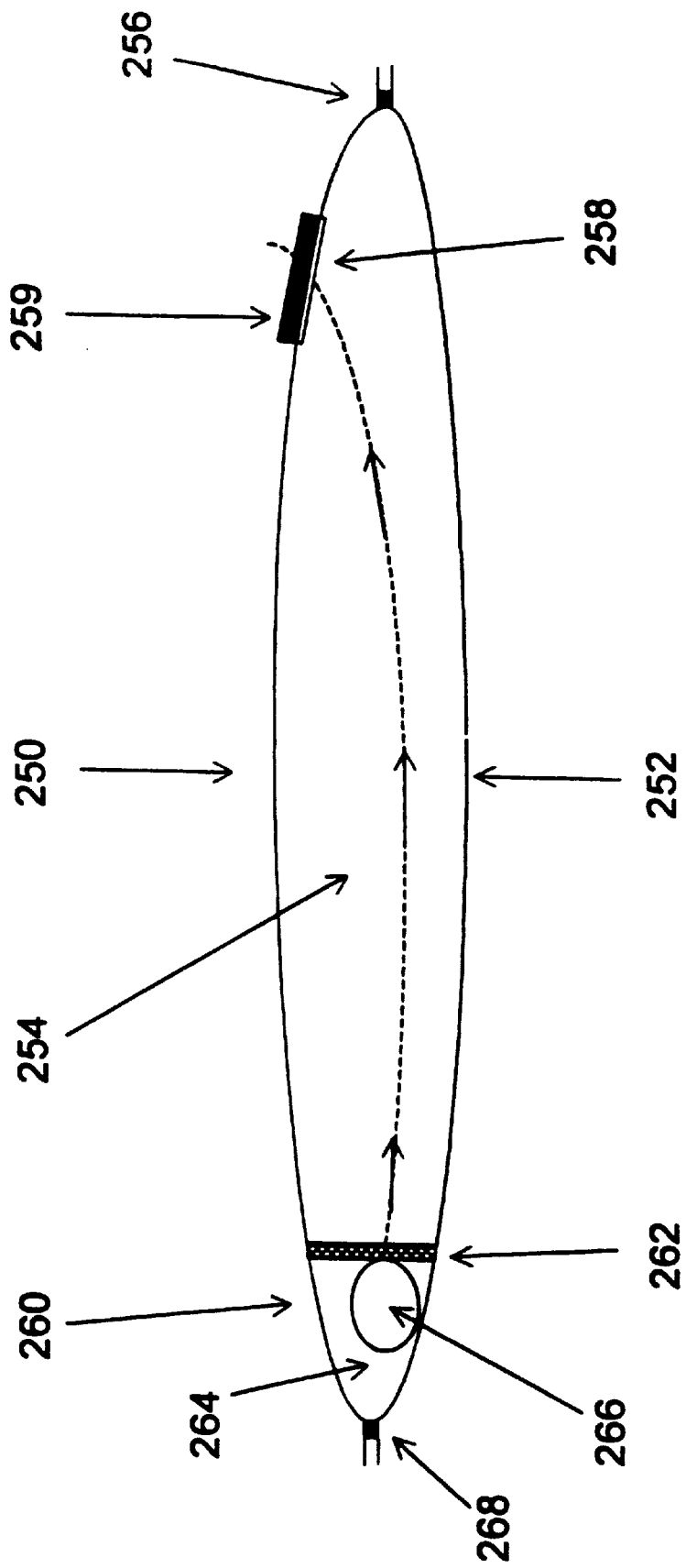
FIG. 9D is a schematic view of another alternative embodiment of the system with one window and sterilant inside a pouch behind a gas permeable membrane.

As illustrated in FIG. 9D, in a second alternative embodiment, the sterilization system comprises a flexible enclosed container 250. Similar to the pouch 200 of the previous embodiment, the flexible container 250 also comprises a gas impermeable sheet material 252 (such as those materials given above) defining a container housing 254 and an opening 256 to place articles (not shown) into the container 250. However, in this embodiment, the container 250 comprises only one gas permeable window 258 on which a process monitoring cartridge 259 is placed, and a sterilant enclosure 260 attached to a gas permeable wall portion 262 of the flexible container 250. In this embodiment, the sterilant enclosure 260 is preferably a flexible sterilant enclosure comprising a sterilant housing 264 which is separated from the container housing 254 by the gas permeable wall portion 262. A sterilant source 266 may be placed into the housing 264 through an optional opening 268. This optional opening 268 may be a resealable opening for multiple use of the container 250 or may be a non-resealable opening for a single use. Similar to the previous embodiment, in operation, the sterilant gas released from the sterilant source 266 diffuses through the gas permeable wall portion 262 into the container housing 254, and reaches at the monitoring cartridge 259 (following arrows in FIG. 9D) through the gas permeable window 258.

Figure 10:
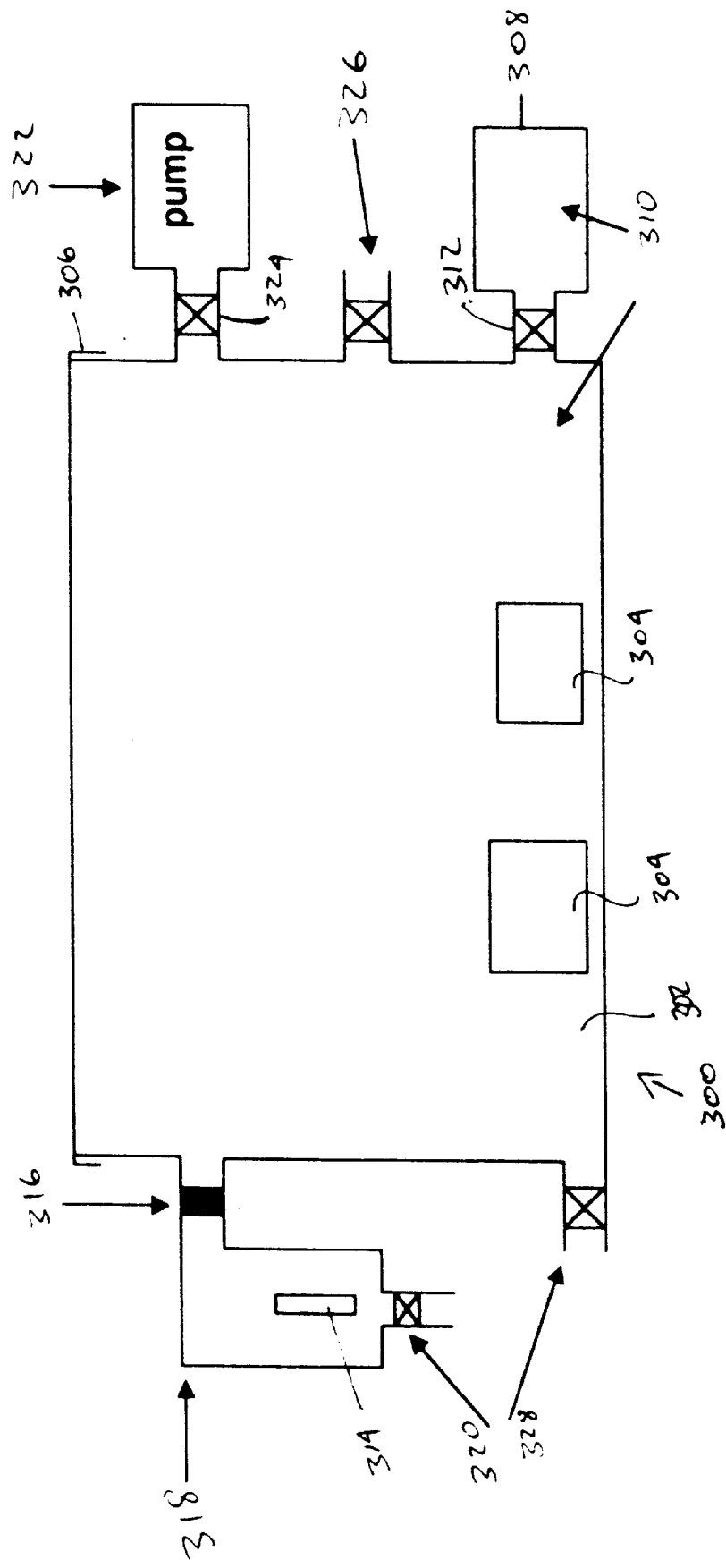
FIG. 10 is a schematic view of a further embodiment of the system.

FIG. 10 illustrates a further embodiment of the invention. A container 300, has an interior space 302, with an article 304 to be sterilized therein. The container 300 may be a rigid container formed of a material suitable for exposure to the sterilization environment, such as a liquid crystal polymer, or may be flexible such as a pouch. So as to protect the sterility or cleanliness of the article 304 or articles, it must be impermeable to microorganisms. The container 300 is shown with a lid 306, but any means of placing the articles 304 into the container 300 and closing them inside as is known in the container art either presently, or during the life of this patent may be employed.

A source 308 of an antimicrobial agent 310 is provided. FIG. 10 shows the source 308 as a separate enclosure attached to the container 300 but most typically the container 300 will be placed into a sterilization chamber (not shown) which is filled with the antimicrobial agent 310, such as a steam sterilizer, or hydrogen peroxide/plasma sterilization chamber as is known in the art. The source 308 is separated from the interior space 302 by a valve 312, thereby allowing ingress of the antimicrobial agent while preventing ingress of microorganisms when the sterilization is completed. Alternatively and preferably, a semi-permeable barrier may be employed.

An indicator 314 is in fluid communication with the interior space 302 past a semipermeable barrier 316 of a vapor permeable, microorganism impermeable material. The indicator 314 is contained within a housing 318 having a valve 320. The entire housing 318 may be detachable from the container 300 or the indicator 314 may be removable from the housing 318. Alternatively, the indicator 314 may connect directly to the container 300 through the barrier 316, thus dispensing with the housing. Of course, a valve could substitute for the barrier 316. Preferably, the indicator 314 is exposed to the antimicrobial agent only through the interior space 302.

The container 300 may comprise the sterilization chamber for purposes of sterlizing the articles 304. FIG. 10 shows the container 300 having a pump 322 connected thereto through an isolation valve 324. The pump 322 draws a vacuum on the interior space 302 which can vaporize a liquid sterilant in fluid communication with the interior space 302 by virtue of being disposed therein or being connected thereto as shown with the source 308. The container 300 may also be used for washing the articles 304 and be provided with a valved fluid inlet 326. A drain valve 328 is also shown. Valves 328 and 320 allow liquid to drain from the container 300 and housing 318.

It will be appreciated that, in all above embodiments, upon completion of the sterilization cycle the process monitor cartridge can be advantageously removed from system to determine chemical and biological efficacy of the sterilization process. As opposed to prior art systems, however, the removal of the biological and chemical indicators does not disturb the sterilized state of the articles inside the sterilization container. Since the gas permeable layer only allows the passage of the sterilant vapor, removal of the cartridge from the sterilizing container will not break the sealed status of the container.

Hence, although the foregoing description of the preferred embodiment of the present invention has shown, described and pointed out the fundamental novel features of the invention, it will be understood that various omissions, substitutions, and changes in the form of the detail of the apparatus and method as illustrated as well as the uses thereof, may be made by those skilled in the art, without departing from the spirit of the present invention. Consequently, the scope of the present invention should not be limited to the foregoing discussions, but should be defined by the appended claims.

What is claimed is:

1. A system for monitoring a sterilization or disinfection process comprising:
- a container impermeable to microorganisms and having an interior space to receive articles to be sterilized or disinfected;
- an antimicrobial source for providing an antimicrobial agent to said interior space;
- at least one indicator for indicating a parameter relevant to said sterilization or disinfection process and which is detachable from said container; and
- an isolation means between said indicator and said interior space for allowing fluid communication between said interior space, at least during said sterilization or disinfection process, and inhibiting the ingress of microorganisms therethrough, at least after said indicator has been detached from said container, whereby said indicator can be detached from said container without potentially exposing said interior space to microorganisms.

2. The system of claim 1 wherein said antimicrobial source comprises an ingress means for allowing the antimicrobial agent ingress to said container during a sterilization process.

3. The system of claim 2 wherein said ingress means comprises a valve.

4. The system of claim 2 wherein said ingress means comprises a vapor permeable, microorganism impermeable material.

5. The system of claim 1 wherein said antimicrobial source comprises a supply of said antimicrobial agent within said interior space.

6. The system of claim 1 wherein said isolation means comprises a valve.

7. The system of claim 1 wherein said isolation means comprises a vapor permeable, microorganism impermeable material.

8. The system of claim 1 wherein said indicator is a biological indicator.

9. The system of claim 1 wherein said biological indicator contains test microorganisms.

10. The system of claim 1 wherein said indicator is a chemical indicator indicative of a parameter relating to said antimicrobial agent.

11. A method of monitoring a disinfection or sterilization procedure comprising the steps of:
- placing an article to be disinfected or sterilized into an interior space of a container impermeable to microorganisms;
- placing at least one indicator into fluid communication with said interior space while performing said disinfection or sterilization procedure by providing an antimicrobial agent in said interior space;
- detaching said indicator from said container while keeping said interior space isolated from microorganisms;
- indicating by said indicator a parameter relevant to said disinfection or sterilization procedure.

12. A method according to claim 11 comprising the step of passing said antimicrobial agent into said interior space through an ingress means.

13. A method according to claim 12 wherein said ingress means comprises a valve.

14. A method according to claim 12 wherein said ingress means comprises a vapor permeable, microorganism impermeable material.

15. A method of claim 11 wherein said antimicrobial agent is liberated inside of said interior space.

16. A method according to claim 15 wherein said antimicrobial agent is vaporized into said interior space.

17. A method according to claim 11 wherein said indicator is a biological indicator and said biological indicator indicates efficacy of said sterilization or disinfection procedure.

18. A method according to claim 11 wherein said antimicrobial agent is selected from the group consisting of: steam, hydrogen peroxide, peracetic acid, chlorine dioxide, glutaraldehyde and ethylene oxide.

19. A method according to claim 11 wherein said indicator is placed into fluid communication with said interior space through a vapor permeable, microorganism impermeable material.

20. A method according to claim 11 wherein said indicator is placed into fluid communication with said interior space through a valve and said valve is closed prior to detaching said indicator from said container.

* * * * *